United States Patent

Marik et al.

(10) Patent No.: US 8,641,736 B2
(45) Date of Patent: Feb. 4, 2014

(54) VERTEBRAL FASTENER SYSTEM

(75) Inventors: Gregory C. Marik, Collierville, TN (US); Newton H. Metcalf, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 197 days.

(21) Appl. No.: 13/354,591

(22) Filed: Jan. 20, 2012

(65) Prior Publication Data

US 2013/0190821 A1    Jul. 25, 2013

(51) Int. Cl.
*A61B 17/88* (2006.01)

(52) U.S. Cl.
USPC .......................................... 606/263; 606/254

(58) Field of Classification Search
USPC ................................................ 606/250–279
See application file for complete search history.

(56) References Cited

U.S. PATENT DOCUMENTS

| | | | |
|---|---|---|---|
| 6,783,527 | B2 | 8/2004 | Drewry et al. |
| 7,572,280 | B2 | 8/2009 | Dickinson et al. |
| 8,034,085 | B2 | 10/2011 | Slivka et al. |
| 2006/0074419 | A1 | 4/2006 | Taylor et al. |

*Primary Examiner* — Mary Hoffman
*Assistant Examiner* — Tara Carter

(57) ABSTRACT

A spinal correction system comprises a flexible longitudinal element extending between a first end and a second end. At least one fixation element includes a first portion and a second portion. The first portion includes an inner surface that defines a cavity such that the longitudinal element is disposable therein. The second portion is configured for penetrating tissue. A coupling member is engageable with the first portion of the at least one fixation element and the longitudinal element to connect the longitudinal element with the at least one fixation element. The coupling member includes a penetrating element configured to extend through the longitudinal element. A flexible member is disposed between the longitudinal element and the inner surface of the first portion of the at least one fixation element. Methods of use are disclosed.

20 Claims, 6 Drawing Sheets

VERTEBRAL FASTENER SYSTEM

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, for stabilization of a treated section of a spine. This disclosure describes an improvement over these prior art technologies.

SUMMARY

Accordingly, a vertebral fastener system is provided. In one embodiment, in accordance with the principles of the present disclosure, a spinal correction system is provided. The system comprises a flexible longitudinal element extending between a first end and a second end. At least one fixation element includes a first portion and a second portion. The first portion includes an inner surface that defines a cavity such that the longitudinal element is disposable therein. The second portion is configured for penetrating tissue. A coupling member is engageable with the first portion of the at least one fixation element and the longitudinal element to connect the longitudinal element with the at least one fixation element. The coupling member includes a penetrating element configured to extend through the longitudinal element. A flexible member is disposed between the longitudinal element and the inner surface of the first portion of the at least one fixation element.

In one embodiment, the system comprises a flexible tether extending between a first end and a second end. A bone fastener includes a proximal portion and a distal portion configured for penetrating tissue. The proximal portion includes a first arm and a second arm extending from the distal portion. The arms includes an inner surface that defines a cavity such that the tether is disposable therein. A coupling member is engageable with the inner surface such that the coupling member translates to apply an amount of force to the tether for fixation with the bone fastener. The coupling member includes a penetrating element configured to extend through the tether. A flexible member is disposed between the tether and the inner surface such that the flexible member biases the tether relative to the inner surface to maintain the amount of force substantially constant.

In one embodiment, the system comprises a flexible tether extending between a first end and a second end. A first bone fastener is connected with the tether adjacent the first end thereof. The first bone fastener includes a proximal portion and a distal portion configured for penetrating vertebral tissue. The proximal portion includes a pair of spaced apart arms extending from the distal portion. The arms include a threaded inner surface that defines a cavity such that the tether is disposable therein. A screw is engageable with the inner surface such that the screw is rotatable to axially translate and apply an amount of force in a transverse orientation to the tether for fixation with the first bone fastener. The screw includes a penetrating element having a sharpened distal tip configured to extend through the tether, A resilient biasing member is disposed between the tether and the inner surface such that the biasing member is configured to adapt to force changes applied to the tether and biases the tether relative to the inner surface to maintain the amount of force substantially constant. A second hone fastener is connected with the tether adjacent the second end thereof.

BRIEF DESCRIPTION OF THE DRAWINGS

The present disclosure will become more readily apparent from the specific description accompanied by the following drawings, in which.

Like reference numerals indicate similar pails throughout the figures.

DETAILED DESCRIPTION

Figure 1:
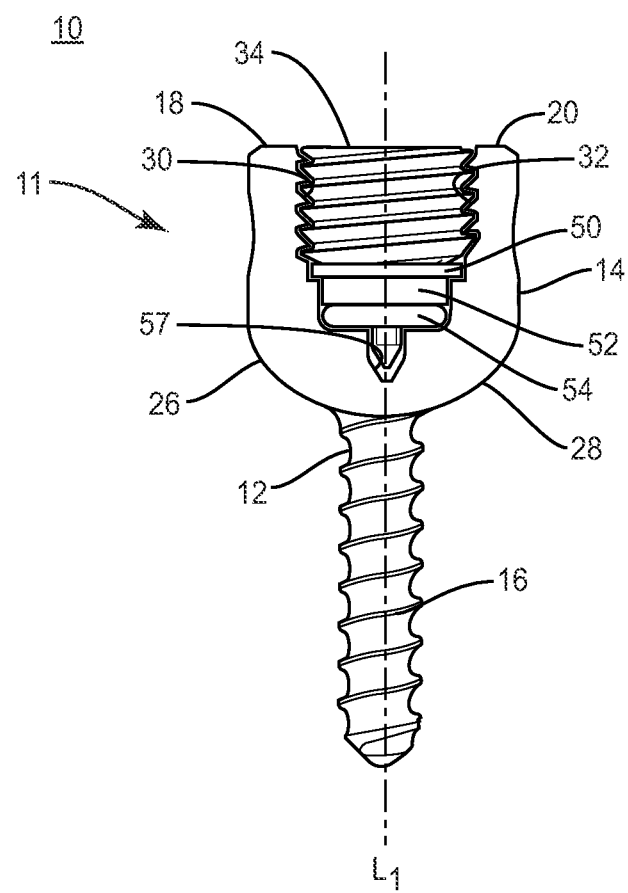
FIG. 1 is a perspective view of one particular embodiment of a vertebral fastener system in accordance with the principles of the present disclosure.
Figure 2:
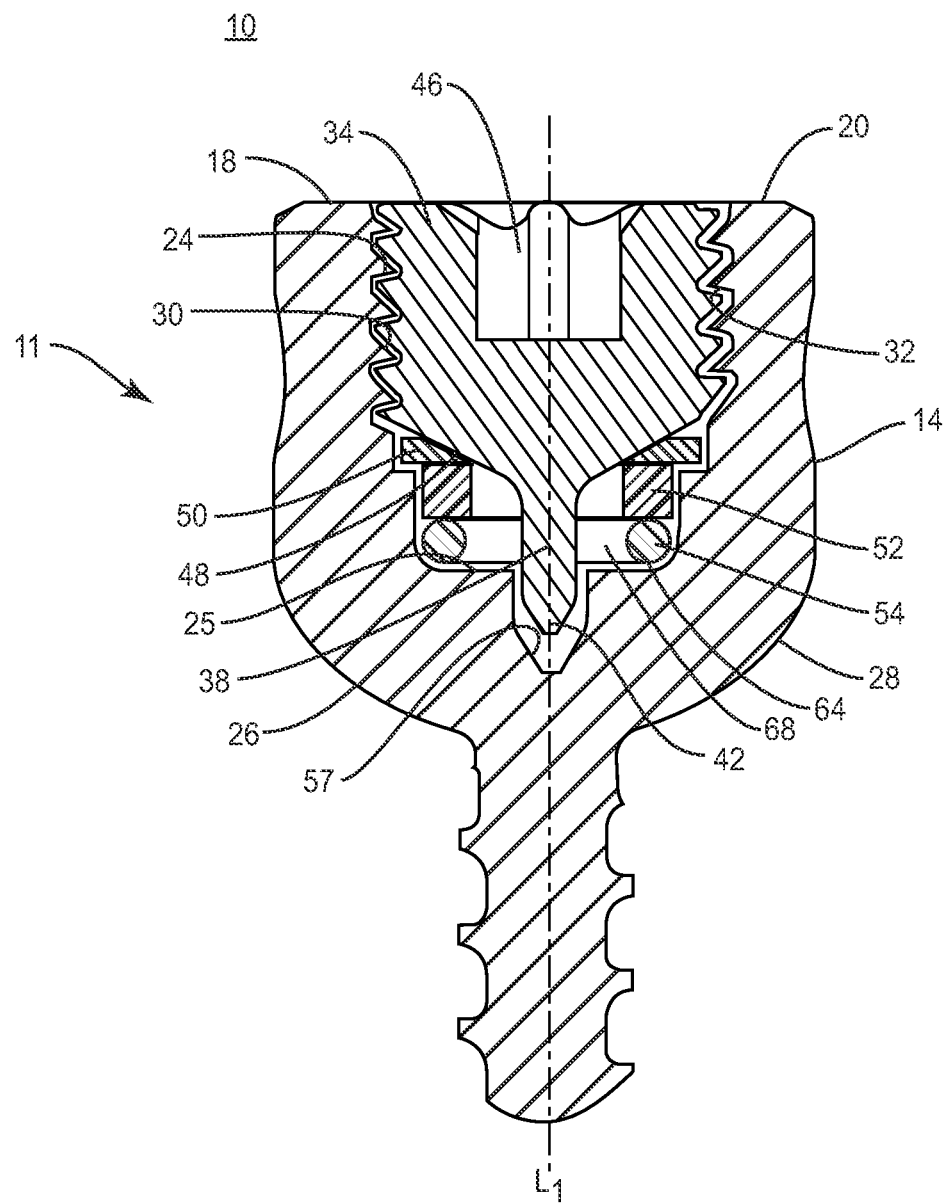
FIG. 2 is a cross-sectional view of the system shown in FIG. 1.

The exemplary embodiments of the vertebral fastener system and related methods of use are discussed in terms of medical devices for the treatment of musculoskeletal disorders and more particularly, in terms of a spinal correction system. It is envisioned that the spinal correction system may be employed in applications for correction of deformities, such as scoliosis, with a device for applying a constant load to a flexible longitudinal element.

In one embodiment, the spinal correction system provides a fixation element and/or a connector to apply a constant load to a flexible longitudinal element. It is envisioned that the configuration of the components of the system maintain a constant load with the flexible longitudinal element in the event the flexible longitudinal element creeps or deforms, including those applications that require application of a constant load over a duration of time.

In one embodiment, the spinal correction system includes a deformable compliant material or resilient member, such as, for example, a spring disposed in a bottom of a fixation element and/or a connector to maintain application of a constant load at the connection with the flexible longitudinal element. For example, the system can be used with a flexible longitudinal element such as a tether in the event the tether material deforms or rips. It is contemplated that one or all of the components of the spinal correction system may be disposable, peel-pack, pre-packed sterile devices. One or all of the components of the system may be reusable. The system may be configured as a kit with multiple sized and configured components.

In one embodiment, the spinal correction system includes an anchor and a set screw including a penetrating member that penetrates a tether material and a washer. The load applied to the tether is dispersed over the body of the washer and a base of the anchor head, which includes a compliant member, such as, for example, a spring. The spring enables the holding force on the tether to remain relatively constant despite growth of a patient and changes to the surgical system.

It is envisioned that the present disclosure may be employed to treat spinal disorders such as, thr example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soil tissue, ligaments, tendons, cartilage and/or bone unless specifically referred to otherwise.

The following discussion includes a description of a spinal correction system in accordance with the principles of the present disclosure. Alternate embodiments are also disclosed. Reference will now be made in detail to the exemplary embodiments of the present disclosure, which are illustrated in the accompanying figures. Turning now to FIGS. 1-5, there is illustrated components of a system, such as, for example, a spinal correction system 10 in accordance with the principles of the present disclosure.

The components of spinal correction system 10 can be fabricated from biologically acceptable materials suitable for medical applications, including metals, synthetic polymers, ceramics, bone material, tissue and/or their composites, depending on the particular application and/or preference of a medical practitioner. For example, the components of spinal correction system 10, individually or collectively, can be fabricated from materials such as stainless steel alloys, commercially pure titanium, titanium alloys. Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplactohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 is employed, for example, with an open, mini-open or minimally invasive surgical technique to attach a longitudinal element to a first side, such as, for example, a convex side of a spine that has a spinal disorder. In one embodiment, the longitudinal element may be affixed to the convex side of each of a plurality of vertebrae such that system 10 prevents growth of vertebrae of a selected section of the spine while allowing for growth and adjustments to a second side, such as, for example, a concave side of the plurality of vertebrae for a correction treatment to treat various spine pathologies, such as, for example, adolescent idiopathic scoliosis and Scheuermann's kyphosis.

Spinal correction system 10 includes at least one fixation element, such as, for example, a bone fastener 11. Bone fastener 11 has a length extending along longitudinal axis L1. Bone fastener 11 comprises a first portion, such as, for example, a head 14 and a second portion, such as, for example, an elongated shaft 12 configured for penetrating tissue. It is envisioned that spinal correction system 10 may include one or a plurality of fixation elements.

Shaft 12 has a cylindrical cross section configuration and includes an outer surface having an external threaded form 16. It is contemplated that thread form 16 may include a single thread turn or a plurality of discrete threads. It is further contemplated that other engaging structures may be located on shaft 12, such as, for example, a nail configuration, barbs, expanding elements, raised elements and/or spikes to facilitate engagement of shaft 12 with tissue, such as, thr example, vertebrae.

It is envisioned that all or only a portion of shaft 12 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 12 may include one or a plurality of openings. It is contemplated that all or only a portion of the outer surface of shaft 12 may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 12 may be disposed at alternate orientations, relative to axis L1, such as, for example, transverse, perpendicular and/or other angular orientations such as acute or obtuse, co-axial and/or may be offset or staggered. It is further envisioned that all or only a portion of shaft 12 may be cannulated.

Head 14 defines an inner surface that includes a wall surface 24 and a base surface 25. The inner surface of head 14 defines a cavity, such as, for example, a U-shaped passageway 22. Head 14 has a first arm 18 and a second arm 20 extending proximally from shaft 12 along axis L1. Arms 18, 20 include wall surface 24 and define at least a portion of U-shaped passage 22. Arm 18 includes an arcuate outer surface 26 and arm 20 includes an arcuate outer surface 28.

It is envisioned that all or only a portion of passageway 22 may have alternate cross section configurations, such as, for example, oval, oblong, triangular, square, polygonal, irregular, uniform, nonuniform, offset, staggered, and/or tapered. It is contemplated that arm 18 and/or arm 20 may include one or a plurality of openings. It is envisioned that arm 18 and/or arm 20 may be disposed at alternate orientations, relative to axis L1, such as, for example, transverse, perpendicular and/or other angular orientations such as acute or obtuse, co-axial and/or may be offset or staggered.

Wall surface 24 includes a thread form 30 located adjacent first arm 18 and a thread form 32 located adjacent second arm 20. Thread forms 30, 32 are configured for engagement with a coupling member, as will be described. In one embodiment, outer surfaces 26, 28 may include a recess or cavity configured to receive an insertion tool, compression instrument and/or instruments for inserting and tensioning bone fastener 11. It is envisioned that wall surface 24 may be disposed with the coupling member in alternate fixation configurations, such as, for example, friction fit, pressure fit, locking protrusion/recess, locking keyway and/or adhesive. It is contemplated that all or only a portion of wall surface 24 may have alternate surface configurations to enhance fixation with the coupling member such as, for example, rough, arcuate, undulating, mesh, porous, semi-porous, dimpled and/or textured according to the requirements of a particular application.

Figure 4:
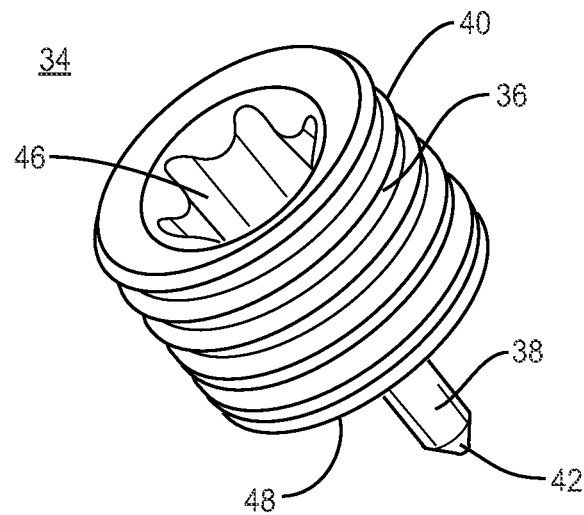
FIG. 4 is a perspective view of a component of the system shown in FIG. 1.
Figure 5:
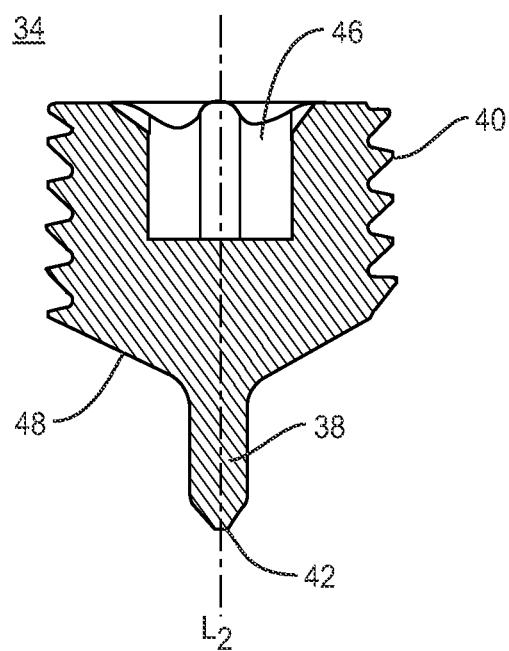
FIG. 5 is a cross-sectional view of the component shown in FIG. 4.

Spinal correction system 10 includes a coupling member, such as, for example, a screw 34, as shown in FIGS. 4 and 5. Screw 34 has a length extending along longitudinal axis L2 and comprises a plug body 36 that is engageable with the inner surface of head 14. A thread form 40 is formed circumferentially about plug body 36. Thread form 40 has a thread run-out (not shown) on a bearing surface 48. Thread form 40 threadably engages forms 30, 32 to attach, fix and/or lock components of spinal correction system 10 with bone fastener 11, as described. Plug body 36 includes a tool receptacle 46 configured to receive a driving tool to apply a rotary driving force to screw 34 to engage screw 34 to thread forms 30, 32 of bone fastener 11.

Figure 3:
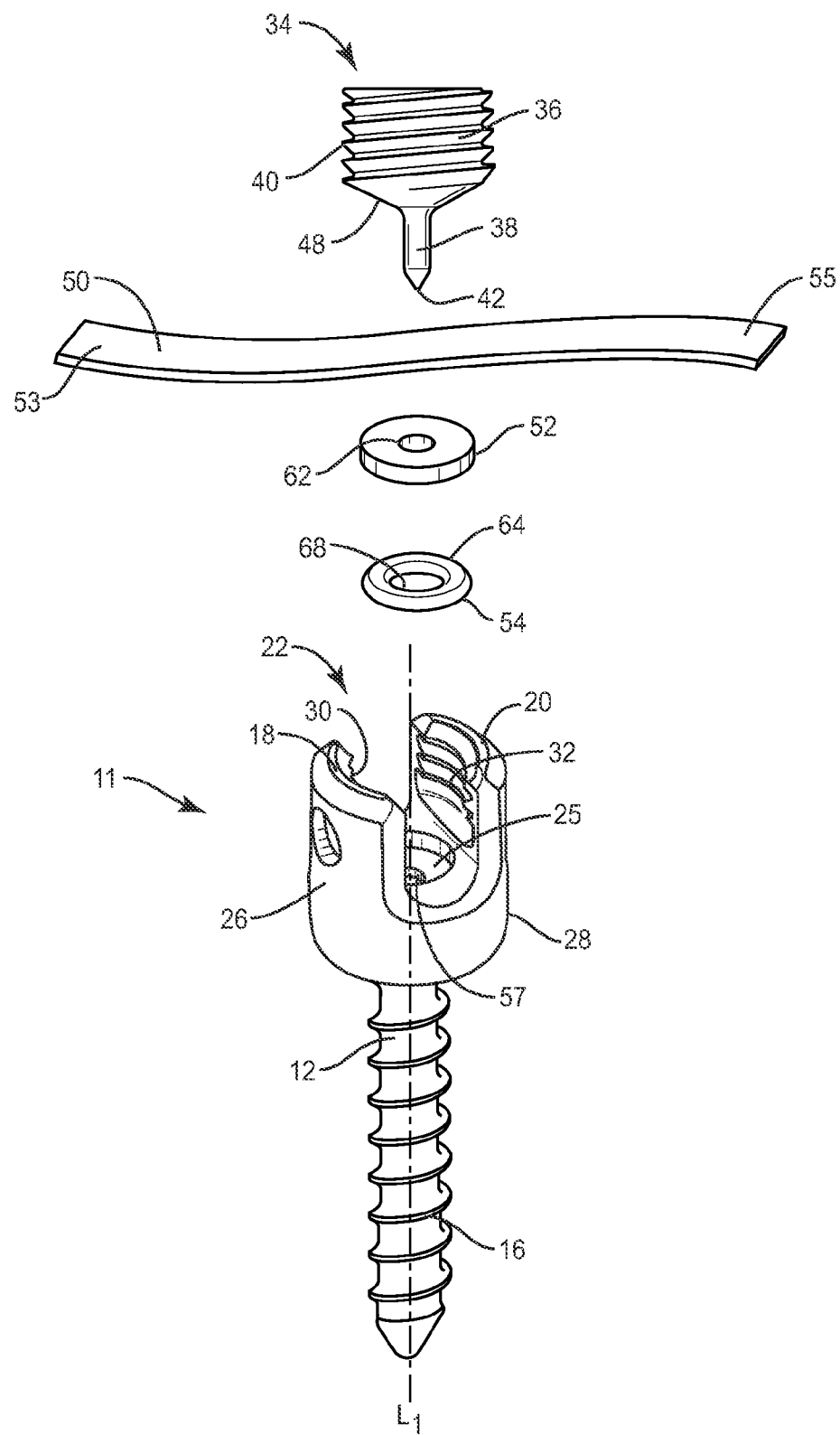
FIG. 3 is a perspective view of the components of the system shown in FIG. 1 with parts separated.

Screw 34 includes an elongate penetrating element 38 extending distally from plug body 36. Element 38 includes a lower bearing surface 48, which engages a flexible longitudinal element, such as, for example, a flexible tether 50 that extends between a first end 53 and a second end 55, as shown in FIG. 3 and described below. Penetrating element 38 includes a distal end 42 tapered to facilitate penetration into flexible tether 50 and engagement of bearing surface 48. Base surface 25 defines a recess 57 configured for disposal of distal end 42 in a substantially flush engagement. It is envisioned that distal end 42 may be alternatively disposed in recess 57, such as, for example, fixed, locked, removable, friction fit, pressure fit and/or adhesive. In one embodiment, penetrating element 38 has a sharpened distal tip configured to pierce a surface of tether 50.

Flexible tether 50 has a flexible configuration, which includes movement in a lateral or side to side direction and prevents expanding and/or extension in an axial direction upon fixation with vertebrae, as will be described. It is envisioned that all or only a portion of flexible tether 50 may have a semi-rigid, rigid or elastic configuration, and/or have elastic properties such that flexible tether 50 provides a selective amount of expansion and/or extension in an axial direction. It is further envisioned that flexible tether 50 may be compressible in an axial direction. Flexible tether 50 can include a plurality of separately attachable or connectable portions or sections, such as bands or loops, or may be monolithically formed as a single continuous element.

Flexible tether 50 can have a uniform thickness/diameter. It is envisioned that flexible tether 50 may have various surface configurations, such as, for example, rough, threaded for connection with surgical instruments, arcuate, undulating, porous, semi-porous, dimpled, polished and/or textured according to the requirements of a particular application. It is contemplated that the thickness defined by flexible tether 50 may be uniformly increasing or decreasing, or have alternate diameter dimensions along its length. It is further contemplated that flexible tether 50 may have various cross section configurations, such as, for example, oval, oblong, triangular, rectangular, square, polygonal, irregular, uniform, non-uniform, variable and/or tapered.

It is contemplated that flexible tether 50 may have various lengths, according to the requirements of a particular application. It is further contemplated that flexible tether 50 may be braided, such as a rope, or include a plurality elongated elements to provide a predetermined force resistance. It is envisioned that flexible tether 50 may be made from autograft and/or allograft, as described above, and be configured for resorbable or degradable applications. In one embodiment, the longitudinal element is a cadaver tendon. In one embodiment, the longitudinal element is a tendon that may be harvested, for example, from a patient or donor. It is contemplated that a tendon harvested from a patient may be affixed in remote locations with the patient's body.

In operation, flexible tether 50 is positioned adjacent bone fastener 11 and screw 34. Screw 34 is disposed with bone fastener 11 such that distal end 42 is aligned with recess 57 such that axis L1 is aligned with axis L2. Flexible tether 50 is disposed within passage 22 and adjacent and/or in engagement with the inner surface of bone fastener 11. Screw 34 is aligned with passage 22 between arms 18, 20. Distal end 42 of penetrating element 38 contacts and/or penetrates flexible tether 50. Screw 34 is rotated and thread form 40 threadably engages thread forms 30, 32 such that the screw 34 axially translates and applies an amount of force in a transverse orientation relative to axis L1 for fixation of tether 50 with bone fastener 11.

For example, screw 34 axially translates through head 14 such that bearing surface 48 engages flexible tether 50 and crimps flexible tether 50 between base surface 25 and bearing surface 48. Penetrating element 38 extends completely through flexible tether 50. It is envisioned that flexible tether 50 is fabricated from compressible material and has a reduced cross-sectional area along its crimped portion between base surfaces 25 and bearing surface 48. In one embodiment, penetrating element 38 provides a bearing surface against which flexible tether 50 acts as it is tensioned or compressed with longitudinal forces that would tend to cause flexible member 50 to slip into bone fastener 11. As such, movement of flexible tether 50 in bone fastener 11 is resisted by friction generated between flexible tether 50 and surfaces 25, 48 and/or the bearing support provided by penetrating element 38. In one embodiment, tether 50 includes one or a plurality of preformed openings configured to receive a coupling member.

A washer 52 disposed within passage 22 and between screw 34 and flexible tether 50. Washer 52 includes a central opening 62 configured for disposed of penetrating element 38. Washer 52 is configured to uniformly spread the applied force transmitted from screw 34. It is envisioned that washer 52 spreads the applied force over a larger area and assists in prevention of loosening of a fixation element. It is further envisioned that washer 52 may be coated with an osteoinductive or osteoconductive material to enhance fixation, and/or include one or a plurality of therapeutic agents.

Spinal correction system 10 includes a flexible member, such as, fir example, a resilient biasing member 54. Resilient biasing member 54 includes a surface 64 that defines an opening 68. Member 54 has a toroid configuration and surface 64 is configured to engage washer 52, base surface 25 and wall surface 24. Member 54 is elastic and pliable in a configuration to react to forces applied and/or force changes applied to spinal correction system 10, such as, for example, patient growth, trauma and degeneration, and/or system 10 component creep, deformation, damage and degeneration, to maintain the applied force transmitted from screw 34 substantially constant. Member 54 is configured to adapt to the above force changes applied to the components of spinal correction system 10 with a resilient bias, such as, for example, a responsive spring force against, for example, washer 52, the inner surface of head 14, screw 34 and/or tether 50, to maintain the applied force transmitted from screw 34 substantially constant.

It is contemplated that resilient member 54 facilitates maintenance of a holding force on tether 50 to remain relatively constant despite growth and changes to system 10. In one embodiment, the flexible member includes a coil spring. In one embodiment, the flexible member includes an elastomeric o-ring. In one embodiment, spinal correction system 10 may not include a washer and member 54 directly engages tether 50.

It is contemplated one or a plurality of fixation elements may be employed with a single vertebral level. It is further contemplated that the fixation elements may be engaged with vertebrae in various orientations, such as, for example, series, parallel, offset, staggered and/or alternate vertebral levels. It is envisioned that the fixation elements may include one or a plurality of anchors, tissue penetrating screws, conventional screws, expanding screws, wedges, anchors, buttons, clips, snaps, friction fittings, compressive fittings, expanding rivets, staples, nails, adhesives, posts, fixation plates and/or posts. These fixation elements may be coated with an osteoinductive or osteoconductive material to enhance fixation, and/or include one or a plurality of therapeutic agents.

In assembly, operation and use, a correction system, similar to the system described above, is employed with a surgical procedure, such as, for a correction treatment to treat adolescent idiopathic scoliosis and/or Scheuermann's kyphosis of a spine. It is contemplated that one or all of the components of the spinal correction system can be delivered or implanted as a pre assembled device or can be assembled in situ. The spinal correction system may be completely or partially revised, removed or replaced.

Figure 6:
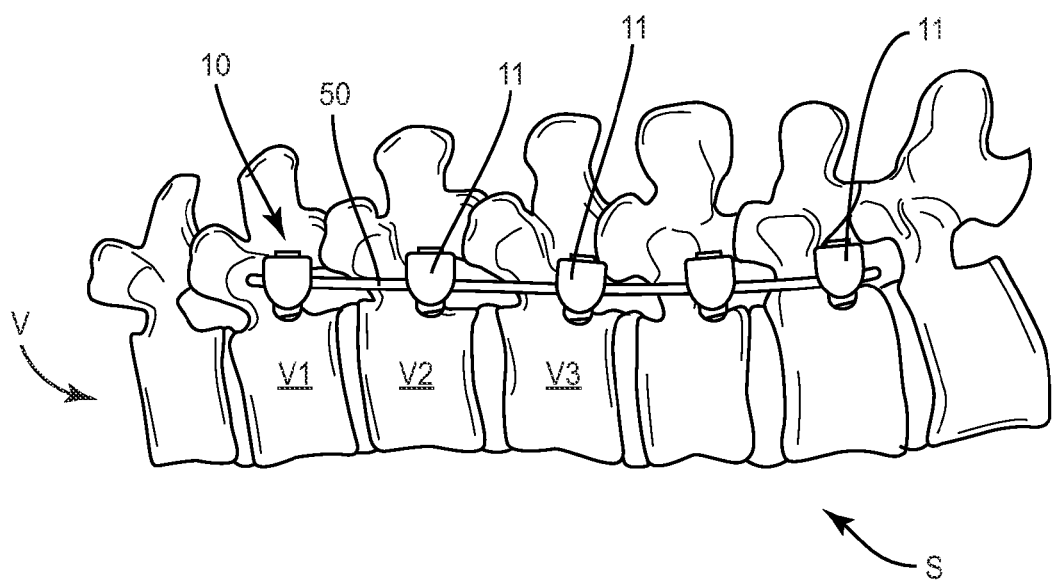
FIG. 6 is a perspective view of one embodiment of a system in accordance with the principles of the present disclosure disposed with vertebrae.
Figure 7:
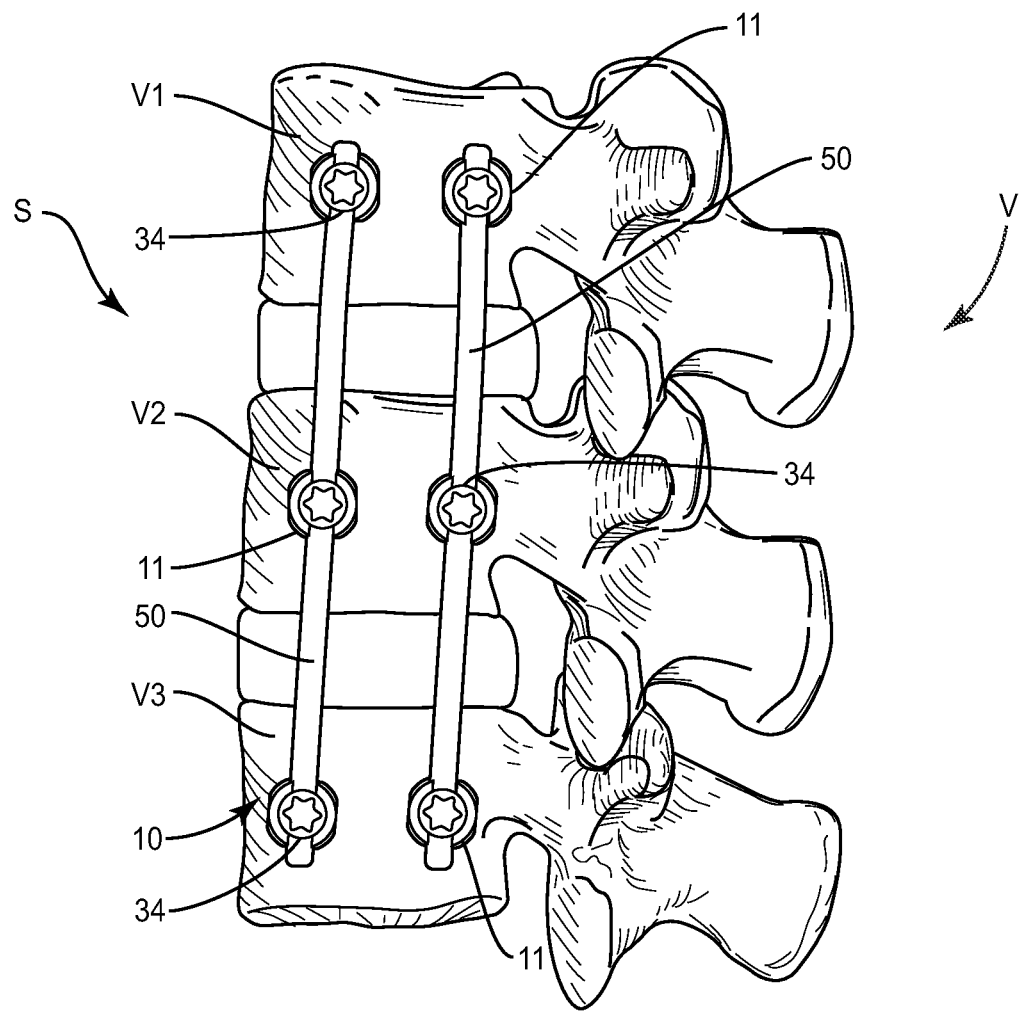
FIG. 7 is a perspective view of the system and vertebrae shown in FIG. 6.

For example, as shown in FIGS. 6 and 7, spinal correction system 10, described above, can be employed with a surgical correction treatment of an applicable condition or injury of an affected section of a spinal column and adjacent areas within a body, such as, for example, at least a first vertebra V1, a second vertebra V2 and a third vertebra V3, of vertebrae V. It is envisioned that spinal correction system 20 may be employed with one or a plurality of vertebrae.

In use, to treat a selected section S of vertebrae V, a medical practitioner obtains access to a surgical site including vertebrae V in any appropriate manner, such as through incision and retraction of tissues. It is envisioned that the spinal correction system can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder. The configuration and dimension of flexible tether 50 is determined according to the configuration and dimension of selected section S and the requirements of a particular application.

An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region according to the requirements of a particular surgical application.

Pilot holes are made in vertebra V1 for receiving shafts 12 of bone fasteners 11. Bone fasteners 11 are delivered along the surgical pathway adjacent vertebra V1 for penetrating engagement with vertebra V1. Each shaft 12 is inserted or otherwise engaged with vertebra V1, according to the particular requirements of the surgical treatment. Bone fasteners 11 are similarly affixed with vertebrae V2, V3.

Other components of spinal correction system 10 are delivered to the surgical site along the surgical pathways, for example, screw 34, tether 50, washer 52 and member 54. These components are disposed with each bone fastener 11, as described above, such that screw 34 is threaded with head 14, and penetrating element 38 passes through the components and tether 50 is fixed with bone fasteners 11 disposed along vertebrae V. Bone fasteners 11 are configured to support a tensile load with tether 50 over selected section S of vertebrae V.

As shown in FIGS. 6 and 7, the components of spinal correction system 10 are attached with a first side, such as, for example, a convex side of vertebrae V to prevent growth of selected section S, while allowing for growth and adjustments to a second side, such as, for example, a concave side of vertebrae V to provide treatment. Compression of section S of vertebrae V occurs along the convex side. As forces and/or force changes are applied to spinal correction system 10, such as, for example, patient growth, trauma and degeneration, and/or system 10 component creep, deformation, damage and degeneration, member 54 adapts with a responsive spring force against washer 52, the inner surface of head 14, screw 34 and/or tether 50, to maintain the applied force transmitted from screw 34 substantially constant.

In one embodiment, spinal correction system 10 includes an agent, which may be disposed, packed or layered within, on or about the components and/or surfaces of the spinal correction system. It is envisioned that the agent may include bone growth promoting material, such as, for example, bone graft to enhance fixation of the fixation elements with vertebrae V.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of spinal correction system 10 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, information and degeneration.

It is envisioned that the use of microsurgical and image guided technologies may be employed to access, view and repair spinal deterioration or damage, with the aid of spinal correction system 10. Upon completion of the procedure, the surgical instruments and assemblies are removed and the incision is closed.

It is contemplated that the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. It is further contemplated that the components of spinal correction system 10 and method of use may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal correction system comprising:
   a flexible longitudinal element extending between a first end and a second end;
   at least one fixation element including a first portion and a second portion, the first portion including an inner surface that defines a cavity such that the flexible longitudinal element is disposable therein, the second portion being configured for penetrating tissue;
   a coupling member engageable with the first portion of the at least one fixation element and the flexible longitudinal element to connect the flexible longitudinal element with the at least one fixation element, the coupling member including a penetrating element configured to extend through the flexible longitudinal element; and
   a flexible member disposed between the flexible longitudinal element and the inner surface of the first portion of the at least one fixation element.

2. A system as recited in claim 1, wherein the flexible longitudinal element includes a tether.

3. A system as recited in claim 1, wherein the flexible longitudinal element includes a cadaver tendon.

4. A system as recited in claim 1, wherein the first portion of the at least one fixation element includes a first arm and a second arm extending from the second portion, the arms including the inner surface that defines the cavity.

5. A system as recited in claim 1, wherein the inner surface defines a recess configured to receive the penetrating element.

6. A system as recited in claim 1, wherein the coupling member engages the inner surface in a configuration to apply a force to the flexible longitudinal element for fixation with the at least one fixation element, the flexible member being pliable to maintain the amount of force substantially constant.

7. A system as recited in claim 1, wherein the coupling member engages the inner surface in a configuration to apply an amount of force in a transverse orientation to the flexible longitudinal element for fixation with the at least one fixation element, the flexible member being pliable to maintain the amount of force substantially constant.

8. A system as recited in claim 1, wherein the flexible member is disposed to bias the flexible longitudinal element relative to the inner surface to maintain the connection of the flexible longitudinal element with the at least one fixation element.

9. A system as recited in claim 1, wherein the coupling member engages the inner surface in a configuration to apply an amount of force in a transverse orientation to the flexible longitudinal element for fixation with the at least one fixation element, the flexible member being disposed to resiliently bias the flexible longitudinal element relative to the inner surface to maintain the amount of force substantially constant.

10. A system as recited in claim 1, wherein the flexible member is a spring.

11. A system as recited in claim 1, wherein the flexible member has a toroid configuration.

12. A system as recited in claim 1, further comprising a washer disposed between the flexible longitudinal element and the flexible member.

13. A system as recited in claim 12, wherein the penetrating element is configured to extend through the washer.

14. A system as recited in claim 1, wherein the flexible longitudinal element includes a plurality of preformed openings, each opening being configured for disposal of the penetrating element.

15. A system as recited in claim 1, wherein the penetrating element includes a sharpened distal tip configured to pierce a surface of the flexible longitudinal element.

16. A spinal correction system comprising:
a flexible tether extending between a first end and a second end;
a bone fastener including a proximal portion and a distal portion configured for penetrating tissue, the proximal portion including a first arm and a second arm extending from the distal portion, the arms including an inner surface that defines a cavity such that the flexible tether is disposable therein;
a coupling member engageable with the inner surface such that the coupling member translated to apply an amount of force to the flexible tether for fixation with the bone fastener, the coupling member including a penetrating element configured to extend through the flexible tether; and a flexible member disposed between the flexible tether and the inner surface such that the flexible member biases the flexible tether relative to the inner surface to maintain the amount of force substantially constant.

17. A system as recited in claim 16, wherein the flexible member is configured to adapt to force changes applied to the flexible tether and biases the flexible tether relative to the inner surface to maintain the amount of force substantially constant.

18. A system as recited in claim 16, wherein the flexible member is a spring.

19. A system as recited in claim 16, further comprising a washer disposed between the flexible tether and the flexible member.

20. A spinal correction system comprising:
a flexible tether extending between a first end and a second end;
a first bone fastener connected with the flexible tether adjacent the first end thereof, the first bone fastener including a proximal portion and a distal portion configured for penetrating vertebral tissue, the proximal portion including a pair of spaced apart arms extending from the distal portion, the arms including a threaded inner surface that defines a cavity such that the flexible tether is disposable therein;
a screw engageable with the inner surface such that the screw is rotatable to axially translate and apply an amount of force in a transverse orientation to the flexible tether for fixation with the first bone fastener, the screw including a penetrating element having a sharpened distal tip configured to extend through the flexible tether; and a resilient biasing member disposed between the flexible tether and the inner surface such that the biasing member is configured to adapt to force changes applied to the flexible tether and biases the flexible tether relative to the inner surface to maintain the amount of force substantially constant; a second bone fastener connected with the tether adjacent the second end thereof.

* * * * *